United States Patent [19]
Kato et al.

[11] Patent Number: 5,665,769
[45] Date of Patent: Sep. 9, 1997

[54] PHARMACEUTICAL COMPOSITION FOR PREVENTING AND TREATING RETINAL DISEASES

[75] Inventors: Kaneyoshi Kato, Kawanishi; Hiroshi Kuriyama, Toyonaka; Hiroaki Naka, Kobe, all of Japan

[73] Assignee: Senju Pharmaceuticals Co., Ltd., Osaka, Japan

[21] Appl. No.: 187,452

[22] Filed: Jan. 28, 1994

[30] Foreign Application Priority Data

Feb. 2, 1993 [JP] Japan .................. 5-015645

[51] Int. Cl.$^6$ .................. A61K 31/34
[52] U.S. Cl. .................. 514/474; 514/912
[58] Field of Search .................. 514/474, 912

[56] References Cited

FOREIGN PATENT DOCUMENTS

| | | |
|---|---|---|
| 0146121 | 6/1985 | European Pat. Off. |
| 0202589 | 11/1985 | European Pat. Off. |
| 0270046 | 6/1988 | European Pat. Off. |

OTHER PUBLICATIONS

K. Kato et al., "Studies on Scavengers of Active Oxygen Species", J. Med. Chem., vol. 31, pp. 793–798, 1988.

M. E. Szabo et al., "Modification of Reperfusion–Induced Ionic Imbalance By Free Radical Scavengers in Spontaneously Hypertensive Rat Retina", Free Radical Biology & Medicine, vol. 13, pp. 609–620.

D. Armstrong et al., "Lipid Peroxidation & Retinopathy in Streptozotocin–Induced Diabetes", Free Radical Biology & Medicine, vol. 11, No. 4, pp. 433–436, 1991.

Z.Y. Li et al., "Amelioration of Photic Injury in Rat Retina by Ascorbic Acid: A Histopathological Study", Investigative Ophthalmology & Visual Science, vol. 26, No. 11, pp. 1589–1598, 1985.

Database WPI, Week 9211, Derwent Publications Ltd., AN 92–085896.

J. Crowe et al., "Retinopathy of Prematurity, Intraventricular Hemorrhage, and Oxidative Damage", vol. 77, No. 1, pp. 129–130, 1986.

Tadahisa Hiramitsu, J. Act. Oxyg. Free Rad., vol. 3, No. 4 (1992).

K. Ishikawa et al., "Retinal Ischemia", Folia Ophthalmologica Japonica, vol. 28, pp. 321–325, (1977).

J.E. Dowling et al., "Inherited Retinal Dystrophy in the Rat", J. Cell Biology, vol. 14, pp. 73–109, (1962).

S. Shahinfar et al., "A pathologic study of photoreceptor cell death in retinal photic injury", Cuur. Eye Res., vol. 10, pp. 47–59, (1991).

*Primary Examiner*—Zohreh Fay
*Attorney, Agent, or Firm*—Foley & Lardner

[57] ABSTRACT

There is disclosed a pharmaceutical composition for preventing or treating a retinal disease which comprises a compound of the formula (I):

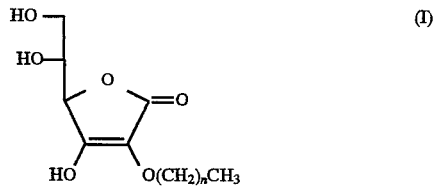

wherein n is an integer of 8 to 20.

11 Claims, 3 Drawing Sheets

PHARMACEUTICAL COMPOSITION FOR PREVENTING AND TREATING RETINAL DISEASES

FIELD OF THE INVENTION

The present invention relates to a pharmaceutical composition for preventing and treating retinal diseases.

BACKGROUND OF THE INVENTION

Retinal diseases are various depending upon their causes of the diseases and modes of the onset of the diseases. Examples of retinal diseases are retinal vascular disorders and inflammatory or degenerative lesions resulting from systemic diseases such as diabetes, hypertension, arteriosclerosis, anemia, leukemia, connective tissue diseases (e.g., systemic lupus erythematosus, scleroderma, etc.), diseases of congenital metabolism anomaly (e.g., Tay-Sachs diseases, Vogt-Spielmeyer diseases, etc.), and, retinal local diseases such as retinal vascular disorders (e.g., retinopathy of prematurity, retinal vein obstruction, retinal artery obstruction, retinal periphlebitis, etc.), retinal inflammations or degeneration derived from retinal detachment or trauma, retinal degenerative diseases accompanying an aging such as senile disciform macular degeneration, congenital retinal degenerative diseases and the like.

Representatives of these retinal diseases are further described below.

Among the retinal diseases resulting from systemic diseases, diabetic retinopathy is recognized as one of the diabetic microangiopathies which are severe complications of diabetes. In the initial stage, capillary microaneurysm and dot hemorrhage are observed. Thereafter, cotton wool patches resulting from microvascular obstruction, and retinal edema, hard exudates or the like resulting from vascular hyperpermeability are observed. Luxuriant changes accompanied by neovascularization appear as the symptoms. In the last stage, retinal detachment is caused by the traction of connective tissues grown in vitreous body. Further, iris rubeosis and neovascular glaucoma are caused, leading to blindness.

Retinae of patients with hypertension manifests hypertensive changes such as arteriolar narrowing or hemorrhage, exudative patches, retinal and optic disk edema and the like; sclerotic changes such as arteriolar sclerosis, arteriovenous crossing phenomena, arterial narrowing, unequal caliber and the like.

Retinal lesions of leukemia include remarkable enlargement of retinal veins, exudation into peri-venous tissue and hemorrhage of various size and shape around the posterior pole. In addition, modular exudate, cotton wool patches resulting from microvascular obstruction, and retinal edema are observed.

Systemic lupus erythematosus is one of the autoimmune diseases manifesting systemic lesions such as eruption, acute nephritis or the like. Retinae of patients with this disease manifest cotton wool patches and sporadic retinal hemorrhage around the posterior pole. In addition, optic disk edema and peripheral vascular inflammation are sometimes observed.

Congenital metabolism anomaly such as the Tay-Sachs disease, Vogt-Spielmeyer disease sometimes exhibits ophthalmopathies as well as systemic symptoms. Typical retinal symptoms are cherry red spots or pigmentary lesions and sometimes complicated by optic nerve atrophy.

Among retinal local diseases, the retinal vein obstruction can be classified into central retinal vein obstruction and branch retinal vein obstruction depending upon the site of the obstruction. The central retinal vein obstruction produces congestion and edema in the optic disk. Blood spots are often observed in the optic disk surface. The retina becomes edematous and manifests cotton wool patches soon. In the branch retinal vein obstruction, radial hemorrhage is seen in the region and retinal edema and cotton wool patches appear.

Also in the retinal artery obstruction, there are central retinal artery obstruction and branch retinal artery obstruction. Soon after artery obstruction occurs, the retina becomes slightly opaque. A few hours later, milk white and edematous retinal opacity is observed and becomes irreversible within 20 to 30 minutes after the obstruction. A few weeks later, the above opacity disappears and the internal layer of the retina is replaced with transparent glia tissues. The obstruction of retinal artery or vein sometimes develops based on hypertension or arteriosclerosis as systemic diseases.

Retinal periphlebitis is an inflammatory disease occurring in the peripheral branches of retinal vein. Findings such as the vein enlargement, bending, unequal caliber, vascular peripheral exudative patches, hemorrhage, neovascularization and the like are observed.

Retinopathy of prematurity is a disease caused when a baby born as a premature infant is housed in a closed incubator and exposed to a high concentration of oxygen. As a result, irreversible obstruction accompanied by vascular endothelial cellular proliferation occurs and later results in neovascularization into vitreous body and retinal detachment.

Retinal detachment is a disease wherein sensory retinae and retinal pigment epithelium are separated. There are rhegmatogenous retinal detachment resulting from retinal tear and secondary retinal detachment occurring in the course of other diseases or resulting from other diseases. These retinal detachments lead to retinal degeneration resulting in blindness unless they are treated by immediate operative therapy such as photocoagulation.

In the senile disciform macular degeneration, neovascularization occurs in the yellow spots from the choroid through Bruch's membrane into under the retinal pigment epithelium. The neogenetic blood vessels grow and also penetrate into subretinal space. The serous exudate from the blood vessels results in retinal pigment epithelium detachment and disciform detachment of the macula. Hemorrhage is repeated mainly in loci containing neogenetic blood vessels and leads to scarring of the foci.

Congenital pigmentary degeneration of the retina occurs in children. Night blindness is observed, and narrowing of visual field and failing of the eyesight gradually proceed. The fundus changes are characterized by pigmentary lesions, yellow atrophy of the optic disk, narrowing of retinal blood vessels, particularly retinal artery.

As methods for treating the various diseases described above, systemic causal therapies may be applied in the case of retinal diseases resulting from systemic diseases. Examples thereof are administration of hypotensive agents against hypertension, administration of hypoglycemic agents against diabetes and the like. However, only these therapies do not always relieve the retinal lesions. Further, in the case of autoimmune diseases and congenital metabolism anomaly, casual therapies are sometimes very difficult or impossible. Treatments for retinal local lesions are therefore required. In this case, pharmacotherapies with vasodilators, vessel wall stabilizers or thromboclastic agents are applied against retinal vascular lesions in diabetes, hypertension or the obstruction of retinal artery or vein. However, these pharmacotherapies are symptomatic and not definitive, and treatment of the diseases often depends upon operative therapies now.

As described above, there is no definitive agent for preventing and treating the above retinal diseases. Under these circumstances, the present inventors have intensively studied to obtain an agent for preventing or treating the above retinal diseases.

As described above, retinal diseases manifest various symptoms including inflammations such as retinal vascular disorders, vascularization, retinal edema, and primary or secondary retinal degeneration and the like. Each disease leads more or less to disorders of retinal functions. Accordingly, the present inventors have advanced investigations from the following two points of view. The first point of view is that the development and progress of the above retinal diseases may be based on or associated with ischemic or hypoxic states and peroxidation induced by the states. The second point of view is that, in view of the special characteristics of retinal functions that eyesight is exhibited by receiving light, excess light itself may be one of the risk factors of these retinal diseases.

With regard to the first point of view, the theory which has become powerful recently is that vascular lesions in diabetic retinopathy are reactions to hypoxic or ischemic states of tissues. Further, there is a report that the lipidperoxide level in the serum of patients was increased by peroxidation considered to be induced by ischemia (Kiyoshi Ishikawa, Masayuki Oshitari et al., Lipidperoxides and retinal ischemia in diabetic retinopathy (I), Folia Ophthalmologica Japonica 28:321–325 (1977)). Furthermore, retinal arteriovenous obstruction results in ischemia, and peroxidation is also considered to be associated with this case.

With regard to the second point of view, there is a report that the progress of retinal degeneration was retarded when congenital retinal dystrophic rats were reared in the dark (Dowling, J. E. and Sidman, R. L.: Inherited retinal dystrophy in the rat; J. Cell Biol. 14:73–109 (1962)). In the case of these rats, the retinal degeneration results from errors in the phagocytosis of retinal pigment epithelial cells renewing outer segments of retinal visual cells with visual ability. In the state wherein the metabolic equilibrium is lost, light itself is shown to promote the destruction of visual cells. There is a report that retinal degeneration was caused in normal animals by intensive exposure to light (Shahinfar, S., Edward, D. P. and Tso, M. O. M.: A pathologic study of photoreceptor cell death in retinal photic injury; Cuur. Eye Res. 10:47–59 (1991)). It can be said that excess light is one of the risk factors of retinal diseases.

By the way, the following reports are made recently. The reports are on the synthesis of ascorbic acid derivatives having a substituent at the 2-position and their antioxidative activity (see EP-A-0146121); on improving effects on circulatory systems such as antiarrhythmic activity, anticardiac infarction activity, anti-cerebral infarction activity, prophylactic effect against senile dementia based on its free-radical scavenging activity of the ascorbic acid derivatives (EP-A-0202589); on therapeutic effects against cataract of a part of the above ascorbic acid derivatives and their bioavailability and preparation (see JP-A 63-301818).

From the above two points of view, the present inventors have studied to obtain compounds which inhibit the peroxidation of retinae or retinal disorders caused by light. As a result, it has been found that the compounds described in the above EP-A-0146121 and EP-A-0202589 include compounds having surprisingly excellent both effects described above. Thus, the present invention has been completed.

OBJECTS OF THE INVENTION

The main object of the present invention is to provide a pharmaceutical composition for preventing or treating retinal diseases.

Another object of the present invention is to provide a process for producing the above pharmaceutical composition.

These objects as well as other objects and advantages of the present invention will become apparent to those skilled in the art from the following description with reference to the accompanying drawings.

BRIEF EXPLANATION OF THE DRAWINGS

In FIGS. 1 to 5, the compound (I) is 2-O-octadecylascorbic acid.

SUMMARY OF THE INVENTION

According to the present invention, there is provided a pharmaceutical composition for treating a retinal disease which comprises a compound of the formula (I):

wherein n is an integer of 8 to 20. Hereinafter, the compound of the formula (I) is sometimes referred to as compound (I).

DETAILED DESCRIPTION OF THE INVENTION

In the formula (I) of the compound described above, the integer represented by n is preferably an integer of 9 to 17, particularly preferably 17. The compounds may be any of D-isomers, L-isomers and mixtures of these isomers. In particular, L-isomers are preferred.

The physical and chemical properties and methods of production of the compound (I) are described in detail in EP-A-0146121. The compound (I) has extremely low toxicity as shown in Experiment 3 hereinafter and therefore the pharmaceutical composition for treating retinal diseases of the present invention can safely be administered.

The compound (I), when used as a remedy for retinal diseases, can usually be administered according to per se known methods, for example, orally (e.g., tablets, capsules, granules, etc.) or parenterally (e.g., eye-drops, eye ointments, injections, etc.) in the form of pharmaceutical compositions produced according to per se known methods by mixing it with a per se known pharmaceutically acceptable additives such as carriers, excipients or diluents.

For oral administration, the daily dose of tablets for an adult is usually 10 mg to 500 mg, preferably 50 mg to 250 mg. For example, tablets are usually prepared by the following procedures. The compound (I) is first rendered granular with or without uniform admixture with a diluent (e.g., lactose, etc.), binder (e.g., syrup, gum arabic, gelatin, sorbitol, tragacanth, polyvinylpyrrolidone, etc.), disintegrator (e.g., potato starch, etc.) and other suitable additives. The resultant granules are provided with additives such as a lubricant (e.g., magnesium stearate, talc, polyethylene glycol, silica, etc.), and compressed into a desired shape and size.

These granules are usually prepared by compressing the compound (I) or the above mixtures and crushing to granules, or by adding moistening agent (e.g., sodium lauryl sulfate, etc.) to the compound (I) or the above mixture, granulating and drying. In each dosage form, the composition of the present invention may contain any other pharmacologically active ingredients unless they are unsuited for the purpose of the present invention.

In the case of eye-drops, a compound (I) of about 0.001–3% (w/v), preferably about 0.01–1% (w/v), is added to a basal medium to make an aqueous solution or a suspension. The pH of the eye-drops of this invention is adjusted to about 4 to 10, preferably about 5 to 9.

The eye-drops of the present invention may be sterilized so as to make the final product sterile. The sterilization may be conducted at any step of preparing the eye-drops. For administration, one to a few drops per dose is instilled in the eye with a frequency of 1 to about 4 times a day according to the patient's condition.

Such eye-drops may further contain pharmaceutically acceptable additives such as buffers (e.g., phosphate buffer, borate buffer, citrate buffer, tartrate buffer, acetate buffer, amino acids, etc.), isotonizing agents (e.g., saccharides such as sorbitol, glucose, mannitol, etc.; polyhydric alcohol such as glycerol, polyethylene glycol, propylene glycol, etc.; salts such as sodium chloride, etc), preservatives (e.g., benzalkonium chloride; benzethonium chloride; parahydroxybenzoic acid esters such as methyl parahydroxybenzoate, ethyl parahydroxybenzoate, etc.; benzyl alcohol; phenethyl alcohol; sorbic acid; sorbic acid salts; thimerosal; chlorobutanol; etc.), pH adjusting agents (e.g., hydrochloric acid, acetic acid, phosphoric acid, sodium hydroxide, etc.), thickening agents (e.g., hydroxyethylcellulose, hydroxypropylcellulose, methylcellulose, hydroxypropylmethylcellulose, carboxymethylcellulose and salts thereof, etc.), chelating agents (e.g., sodium edetate, sodium citrate, condensed sodium phosphate, etc.), solubilizers (e.g., ethanol, polyoxyethylene hydrogenated castor oil, polysorbate 80, macrogol 4000, etc.).

An eye ointment is produced by admixing the active ingredient in a concentration of about 0.001 to 3% (w/w), preferably 0.01 to 1% (w/w), with a conventional eye ointment base. When preparing the eye ointment of the present invention, procedures for pulverization of compound (I) and sterilization of the composition are preferable. The eye ointment is administered 1 to about 4 times a day depending on the patient's condition.

As the eye ointment base, there may be mentioned petrolatum, Macrogol and carboxymethylcellulose, among others.

The pharmaceutical composition of the present invention may further contain at least one therapeutically active ingredient against retinal diseases in addition to the compound (I) unless it is unsuited for the purpose of the present invention.

Further, the composition of the present invention may contain any other pharmacologically active ingredients unless they are unsuited for the purpose of the present invention.

As is clear from Experiments described below, the pharmaceutical composition for preventing and treating retinal diseases of the present invention have excellent antioxidative activity (free-radical scavenging activity) and inhibitory activity of retinal disorders caused by light. The composition can therefore be used as a medicament for preventing or treating various retinal diseases including retinal vascular disorders and inflammatory or degenerative lesions resulting from systemic diseases such as diabetes, hypertension, arteriosclerosis, anemia, leukemia, connective tissue diseases (e.g., systemic lupus erythematosus, scleroderma, etc.), diseases of congenital metabolism anomaly (e.g., Tay-Sachs diseases, Vogt-Spielmeyer diseases, etc.), and, retinal local diseases such as retinal vascular disorders (e.g., retinopathy of prematurity, retinal vein obstruction, retinal artery obstruction, retinal periphlebitis, etc.), retinal inflammations or degeneration derived from retinal detachment or trauma, retinal degenerative diseases accompanying an aging such as senile disciform macular degeneration, congenital retinal degenerative diseases and the like.

The following Examples and Experiments further illustrate the present invention in detail but are not to be construed to limit the scope thereof.

EXAMPLE 1

| Tablet: | |
|---|---|
| 2-O-octadecylascorbic acid | 50 g |
| corn starch | 90 g |
| lactose | 25 g |
| hydroxypropylcellulose | 25 g |
| magnesium stearate | 5 g |
| total | 195 g |

50 g of 2-O-octadecylascorbic acid was first rendered granular with 90 g corn starch, 25 g of lactose and 25 g of hydroxypropylcellulose. The resultant granules were provided with 5 g of magnesium stearate and compressed into tablets.

One to three tablets per day are administered to an adult.

EXAMPLE 2

| Ophthalmic solution (eye-drops): | (w/v)% |
|---|---|
| 2-O-octadecylascorbic acid | 0.1 |
| boric acid | 1.7 |
| sodium borate | 0.4 |
| sodium edetate | 0.02 |
| benzalkonium chloride | 0.005 |
| sterile purified water ad. | 100.0 |

To 800 ml of sterile purified water were dissolved 17 g of boric acid, 4 g of sodium borate, 0.2 g of sodium edetate and 0.05 g of benzalkonium chloride. To the thus obtained solution was added 1 g of 2-O-octadecylascorbic acid to make an aqueous solution. Then, to this solution was further added sterile purified water to make the total volume 1000 ml. After sterilization by filtration, the solution is filled into eye drop bottles to obtain an ophthalmic solution.

EXAMPLE 3

| Ophthalmic suspension (eye-drops): | (w/v) % |
|---|---|
| 2-O-octadecylascorbic acid | 1.0 |
| polyvinyl alcohol | 0.5 |
| dibasic sodium phosphate (dodecahydrate) | 0.5 |
| monobasic sodium phosphate (dihydrate) | 0.2 |
| disodium edetate | 0.02 |
| sodium chloride | 0.7 |
| benzalkonium chloride | 0.007 |
| sterile purified water ad. | 100.0 |

To about 800 ml of sterile water were dissolved 5 g of polyvinyl alcohol, 5 g of dibasic sodium phosphate, 0.2 g of disodium edetate and 7 g of sodium chloride. After sterilizing the solution by filtration, 10 g of 2-O-octadecylascorbic acid and 0.07 g of benzalkonium chloride were added to the above obtained solution under sterile conditions. Sterile purified water was added with stirring to the total volume of 1000 ml. The suspension thus obtained was filled into eye drop bottles to make an ophthalmic suspension.

EXAMPLE 4

| Eye ointment: | (w/v) % |
|---|---|
| 2-O-octadecylascorbic acid | 0.5 |
| liquid paraffin | 1.0 |
| white petrolatum ad. | 100.0 |

Under sterile conditions, 1 g of sterilized liquid paraffin and 0.5 g of 2-O-octadecylascorbic acid were poured into a mortar and then kneaded (pulverized) thoroughly. To the mixture, white petrolatum was gradually added under kneading to make the total weight 100 g. The product thus obtained was filled into a tube for ophthalmic use to obtain an eye ointment.

EXPERIMENT 1

Effects of 2-O-octadecylascorbic acid on retinal peroxidation induced by ferrous ion:

(A) In vitro experiment using a bovine retinal homogenate:

Effects of 2-O-octadecylascorbic acid on the peroxidation induced by adding ferrous chloride to a bovine retinal homogenate were examined.

Method:

(1) Retinae were removed from bovine eyeballs (½ eye). Physiological saline was added to the retinae to prepare bovine retinal homogenates.

(2) Ferrous chloride (0.5 mM, dissolved in distilled water) was added to each of the retinal homogenates obtained in the above. Further, 2-O-octadecylascorbic acid and α-tocopherol were added to the resulting homogenates to final concentrations of the reaction mixtures of $10^{-4}$M, respectively. Further, distilled water was added to each of the homogenates to adjust a total volume to 1 ml. 2-O-octadecylascorbic acid and α-tocopherol were dissolved and diluted with ethanol. Thus, the final concentrations of ethanol in all of the reaction mixtures were adjusted to 1%. Then, the mixtures were subjected to reaction at 37° C. for 1 hour.

(3) 0.35% thiobarbituric acid (hereinafter referred to as TBA) reagent (50% aqueous acetic acid solution)(1 ml) was added to the reaction mixtures or standard solutions of the retinal homogenates obtained in the above (2). The mixtures were subjected to reaction in boiling water at 100° C. for 1 hour. After water cooling, n-butanol (2 ml) was added, and the mixtures were shaken for 5 minutes and centrifuged at 3000 rpm for 10 minutes. Fluorescence intensities (excitation wave length: 515 nm, emission wave length: 553 nm) were determined for the n-butanol layer. Proteins were determined using Bio-Rad Protein Assay Kit (trade name).

Results:

The results are shown in Table 1.

TABLE 1

| | | Retina: TBA value (nM malondialdehyde/ mg protein) | Inhibitory ratio (%) |
|---|---|---|---|
| Blank (1% ethanol) | | 0.34 ± 0.01 (2) | 100 |
| Ferrous chloride (control) | | 5.65 ± 0.13 (3) | 0 |
| 2-O-octadecyl-ascorbic acid | $10^{-4}$ M | 0.61 ± 0.04 (3) * | 94.9 |
| α-Tocopherol | $10^{-4}$ M | 2.38 ± 0.12 (3) * | 61.6 |

Note: In the above table, each value of "retina: TBA value" is indicated in terms of mean ± S.D.. The numbers in the parentheses after the values represent the sample numbers. The mark "*" indicates that there is a significant difference in comparison with the control. $p < 0.001$.

As is clear from the results in Table 1, addition of ferrous chloride to the bovine retinal homogenates results in about 17-fold increase in the TBA value based on that of the blank. When the reaction was conducted in the presence of 2-O-octadecylascorbic acid, more excellent inhibitory effect on the peroxidation of the retinal homogenate than that in the presence of α-tocopherol was obtained even in a low concentration of $10^{-4}$M.

(B) In vivo experiment in rats by intravitreous injection of ferrous ion:

(B-1) Evaluation by retinal TBA values

Antioxidative effects of oral administration of a suspension of 2-O-octadecylascorbic acid (30 mg/kg) on the retinal peroxidation induced by intravitreous injection of ferrous sulfate in rats were examined.

Method:

Seven weeks old SD rats fasted from the previous day were divided into 2 groups. A 5% solution of gum arabic (control)(2 ml/kg) was administered orally to one group in 3 divided portions. A 1.5% suspension (2 ml/kg) of 2-O-octadecylascorbic acid (30 mg/kg) was administered orally to the other group in 3 divided portions. Two hours after the first administration, rats were anesthetized systemically with ketamine hydrochloride. A 5 mM solution (5 µl) of ferrous sulfate was injected intravitreously into each of the left eyes, and physiological saline (5 µl) was injected intravitreously into each of the right eyes. Each injection was carried out using a microsyringe. One and four hours after the injection, a suspension of 2-O-octadecylascorbic acid or a 5% solution of gum arabic were administered again. Two hours after the third administration (i.e. six hours after the injection of ferrous ion), the rats were sacrificed. The eyeballs were removed, retinal homogenates were prepared from the eyes, and the TBA values and protein were determined.

Results:

The results are shown in Table 2.

TABLE 2

|  | Retina: TBA value (nM malondialdehyde/mg protein) | |
| --- | --- | --- |
|  | Right eye | Left eye |
| Gum arabic solution (control) | 0.48 ± 0.14 (5) | 0.65 ± 0.06 (5) |
| 1.5% 2-O-octadecyl-ascorbic acid suspension | 0.36 ± 0.06 (6) | 0.47 ± 0.11 (6)* |

Note: In the above table, each value of "retina: TBA value" is indicated in terms of mean ± S.D.. The numbers in the parentheses after the values represent the sample numbers. The mark "*" indicates that there is a significant difference in comparison with the control. $p < 0.01$.

As is clear from the results in Table 2, the oral administration of a 1.5% suspension of 2-O-octadecylascorbic acid (30 mg/kg) significantly inhibited the increase in the TBA value of the retina induced by intravitreous injection of ferrous ion. In the 5% gum arabic administered group, intravitreous profuse hemorrhage probably occurring during the injection was observed in two eyes of five eyes into which physiological saline was injected. Their TBA values were higher than those of the other eyes into which physiological saline was injected.

(B-2) Evaluation by Electroretinogram (hereinafter referred to as ERG) determination Effects of oral administration of 2-O-octadecylascorbic acid (30 mg/kg) on the changes of ERG induced by intravitreous injection of ferrous sulfate in rats were examined.

Method:

Twelve SD rats (7 weeks old) were fasted from the previous day. A 7.5 mM ferrous sulfate (5 µl) solution was injected intravitreously into each of the left eyes. A 1.5% suspension of 2-O-octadecylascorbic acid (30 mg/kg) or a 5% solution of gum arabic (control) was firstly administered orally 2 hours before the ferrous ion injection, and thereafter administered three times every 3 hours and then three times every 5 hours. ERG was determined 6, 9 and 24 hours after the ferrous ion injection and evaluated for the latency and amplitude of a-wave and b-wave.

Figure 1:
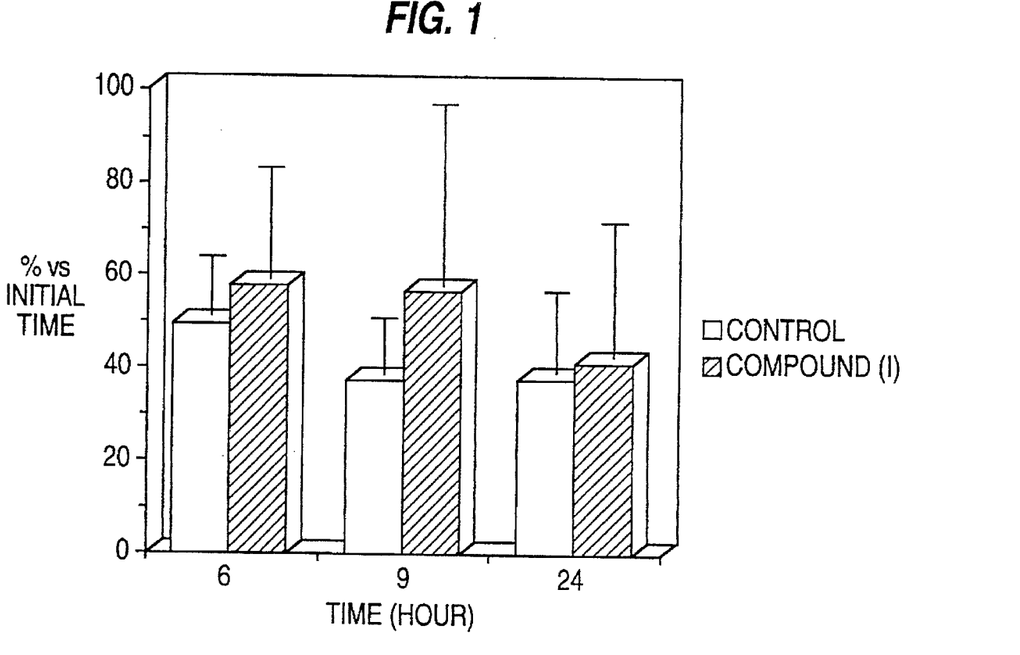
FIG. 1 is a graph showing the a-wave amplitude of ERG in rats after intravitreous injection of ferrous ion in Experiment 1 (B-2). The abscissa indicates time (hour) and the ordinate indicates percentage (%) relative to the initial amplitude.
Figure 2:
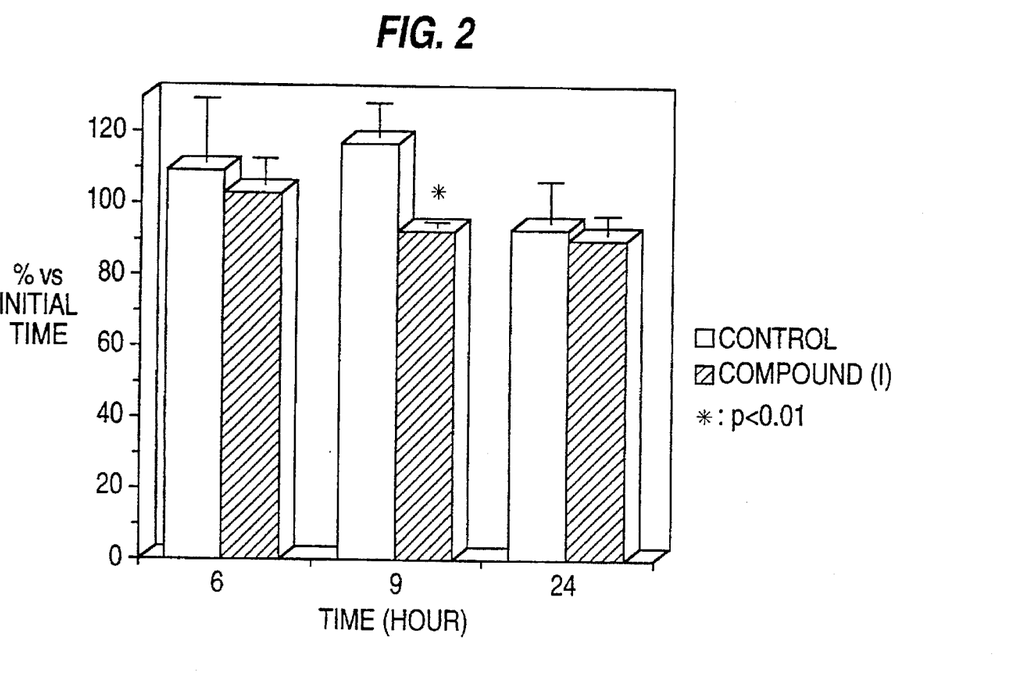
FIG. 2 is a graph showing the b-wave latency of ERG in rats after intravitreous injection of ferrous ion in Experiment 1 (B-2). The abscissa indicates time (hour) and the ordinate indicates percentage (%) relative to the initial amplitude.
Figure 3:
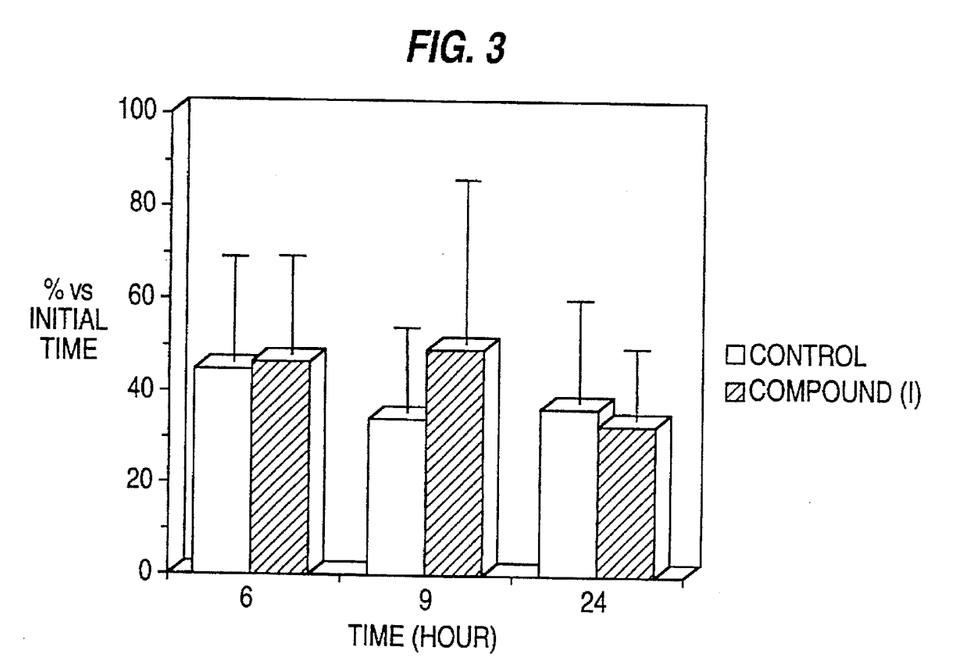
FIG. 3 is a graph showing the b-wave amplitude of ERG in rats after intravitreous injection of ferrous ion in Experiment 1 (B-2). The abscissa indicates time (hour) and the ordinate indicates percentage (%) relative to the initial amplitude.

Results:

The results of the ERG determination in rats after the intravitreous injection of ferrous ion are shown in FIG. 1 (a-wave amplitude of ERG in rats after intravitreous injection of ferrous ion), FIG. 2 (b-wave latency of ERG in rats after intravitreous injection of ferrous ion) and FIG. 3 (b-wave amplitude of ERG in rats after intravitreous injection of ferrous ion).

As a result, delay of the latency and decrease of the amplitude of a-wave and b-wave were strongly observed in both groups from 6 hours after the ferrous ion injection. The amplitude was not recovered even in the determination after 24 hours. A more marked tendency to inhibit the decrease of the amplitude of a-wave and b-wave was observed in the determination 9 hours after the ferrous ion injection in the 2-O-octadecylascorbic acid suspension administered groups compared to the control group, and the delay of the b-wave latency was significantly inhibited (cf. FIGS. 1 to 3).

Discussion:

The above results show that, because of the inhibitory activity against retinal peroxidation and ERG changes caused by ferrous ion, 2-O-octadecylascorbic acid is useful for prevention and treatment of various retinal diseases resulting from retinal peroxidation including retinal vascular disorders and inflammatory or degenerative lesions resulting from systemic diseases such as diabetes, hypertension, arteriosclerosis, anemia, leukemia, connective tissue diseases (e.g., systemic lupus erythematosus, scleroderma, etc.), diseases of congenital metabolism anomaly (e.g., Tay-Sachs diseases, Vogt-Spielmeyer diseases, etc.), and, retinal local diseases such as retinal vascular disorders (e.g., retinopathy of prematurity, retinal vein obstruction, retinal artery obstruction, retinal periphlebitis, etc.), retinal inflammations or degeneration derived from retinal detachment or trauma, retinal degenerative diseases accompanying an aging such as senile disciform macular degeneration, congenital retinal degenerative diseases and the like.

EXPERIMENT 2

Examination of effects of 2-O-octadecylascorbic acid on retinal disorders caused by light (A) In vitro experiment using bovine retinal homogenates Antioxidative effects of 2-O-octadecylascorbic acid on peroxidation caused by light exposure of bovine retinal homogenates in the presence of hematoporphyrin (hereinafter referred to as HPP) were examined.

Method:

(1) HPP (100 µM, dissolved in ethanol), 2-O-octadecylascorbic acid ($10^{-4}$M) and water were added to a retinal homogenate prepared by the same manner as that of the above Experiment 1 (A) Method (1). The mixture was irradiated with a fluorescent lamp (daylight lamp, 15 W, 3000 lux) from 20 cm above for 1 hour. The final concentration of ethanol in the reaction mixture was adjusted to 2%.

(2) One hour after the light exposure, according to the same manner as that of the above Experiment 1 (A) Method (3), lipidperoxides were determined by the TBA reaction and proteins were determined using Bio-Rad Protein Assay Kit (trade name).

Method:

The results are shown in Table 3.

TABLE 3

|  | Retina: TBA value (nM malondialdehyde/ mg protein) | Inhibitory ratio (%) |
| --- | --- | --- |
| Blank (HPP, 1% ethanol) | 0.59 ± 0.10 (3) | 100 |
| HPP, light (control) | 2.22 ± 0.06 (3) | 0 |
| 2-O-octadecyl-ascorbic acid ($10^{-4}$ M) | 1.31 ± 0.21 (3) * | 55.8 |

TABLE 3-continued

| | Retina: TBA value (nM malondialdehyde/ mg protein) | Inhibitory ratio (%) |
|---|---|---|

Note: In the above table, each value of "retina: TBA value" is indicated in terms of mean ±S.D.. The numbers in the parentheses after the values represent the sample numbers. The mark "*" indicates that there is a significant difference in comparison with the control. $p < 0.001$.

As is clear from the results in Table 3, addition of HPP to the bovine retinal homogenates followed by light exposure resulted in about 4-fold increase in the TBA value based on that of the blank. When the reaction was conducted in the presence of a suspension of 2-O-octadecylascorbic acid, significant inhibitory effect was observed in a concentration of $10^{-4}M$ (inhibitory ratio: about 56%).

(B) In vivo experiment by light exposure in rats (B-1) Evaluation by retinal pathological tissues and rhodopsin amount Method:

Rats were subjected to dark adaptation for 72 hours. Then the rats were irradiated continuously for 12 hours using a green fluorescent lamp (10 W, 490–580 nm), the illumination intensity of which was adjusted to 2000 to 2400 lux. A suspension of 1.5% or 5.0% 2-O-octadecylascorbic acid was orally administered three times a day (90, 300 mg/kg/day) on the day of light exposure, and once a day (30, 100 mg/kg/day) after that. To the control group was administered 5.0% gum arabic solution (control) according to the same schedule. After completion of the light exposure, the rats were reared in a dark room and sacrificed on the 5th day. The right eyes were marked with ink in the upper part and fixed with 2% paraformaldehyde and 2% glutaraldehyde solutions. Histopathological evaluation was made using a light microscope and the thickness of retinae (thickness of retinal entire layer and outer nuclear layer) was measured. The left eyes were stored under freezing conditions at −20° C. for rhodopsin determination after removal of the cornea, lens and vitreous body.

Rhodopsin was determined as follows. Firstly, the optic cup was sliced under a red lamp in a dark room, and retinal homogenates were prepared using 0.1M phosphate buffer (pH 7.2). After centrifugation at 15,000 rpm for 15 minutes, the precipitation was treated with 4% potassium alum solution. After washing, rhodopsin was extracted with 1% Emulphogen BC-720 (trade mark). The absorbance at 500 nm was measured using the centrifuged supernatant as the sample. The sample was bleached by light exposure with a yellow lamp for 5 minutes. The absorbance at 500 nm was measured again. The rhodopsin amount was calculated from the difference between the absorbances before and after the bleach (molar absorption coefficient: 42,000).

Results:

The results of the histopathological evaluation with a light microscope are shown in Table 4 (5.0% gum arabic solution), Table 5 (1.5% 2-O-octadecylascorbic acid suspension) and Table 6 (5.0% 2-O-octadecylascorbic acid suspension). The marks in Tables 4 to 6 have the following meanings.

TABLE 4

| 5.0% gum arabic solution (control) | | | | | |
|---|---|---|---|---|---|
| Animal No. | 1 | 2 | 3 | 4 | 5 |
| Vacuolation of retinal pigment epithelium | + | + | + | + | + |
| Disarrangement or vacuolation of inner and outer segments of visual cells | + | ++ | ++ | ++ | ++ |
| Infiltration of macrophage | + | ++ | ++ | ++ | ++ |
| Pyknosis and nuclear disappearance in outer nuclear layer | + | ++ | ++ | ++ | ++ |
| Thinning of retinal entire layer | − | ++ | ++ | ++ | ++ |

−: not observable, ±: slightly observable
+: observable, ++: remarkably observable

TABLE 5

| 1.5% 2-O-octadecylascorbic acid suspension | | | | | |
|---|---|---|---|---|---|
| Animal No. | 1 | 2 | 3 | 4 | 5 |
| Vacuolation of retinal pigment epithelium | + | + | + | + | + |
| Disarrangement or vacuolation of inner and outer segments of visual cells | ++ | ++ | + | ++ | ++ |
| Infiltration of macrophage | ++ | ++ | − | ++ | ++ |
| Pyknosis and nuclear disappearance in outer nuclear layer | ++ | ++ | ± | ++ | ++ |
| Thinning of retinal entire layer | ++ | ++ | − | ++ | ++ |

TABLE 6

| 5.0% 2-O-octadecylascorbic acid suspension | | | |
|---|---|---|---|
| Animal No. | 1 | 2 | 3 |
| Vacuolation of retinal pigment epithelium | − | + | + |
| Disarrangement or vacuolation of inner and outer segments of visual cells | ± | + | ++ |
| Infiltration of macrophage | − | − | ++ |
| Pyknosis and nuclear disappearance in outer nuclear layer | ± | + | ++ |
| Thinning of retinal entire layer | − | + | ++ |

As is clear from the results shown in Tables 4 to 6, in the retinal lesions caused by light exposure, the pyknosis and nuclear disappearance in the outer nuclear layer, the disarrangement and vacuolation of inner and outer segments of visual cells, the infiltration of macrophage into the outer segments and the thinning of retinal entire layer were remarkably observed in four of five examples in each of the control group and 1.5% 2-O-octadecylascorbic acid suspension administered group and in one of three examples of the 5.0% 2-O-octadecylascorbic acid suspension administered group. That is, the lesions in the 5.0% 2-O-octadecylascorbic acid suspension administered group were not so severe as those of the control group.

Table 7 and Table 8 show the results of the measurement of the thickness of retinal entire layer and outer nuclear layer, respectively.

TABLE 7

| | Thickness of retinal entire layer (μM) | |
|---|---|---|
| | Lesion | Near optic disk |
| Gum arabic solution (control) | 81.5 ± 6.5 (5) | 121.0 ± 15.9 (5) |
| 1.5% 2-O-octadecyl-ascorbic acid suspension | 88.5 ± 22.3 (5) | 135.5 ± 27.9 (5) |
| 5.0% 2-O-octadecyl-ascorbic acid suspension | 84.2 ± 16.3 (3) | 161.7 ± 3.8 (3)* |

Note: In the above table, each value of "thickness of retinal entire layer" is indicated in terms of mean ± S.D.. The numbers in the parentheses after the values represent the sample numbers. The mark "*" indicates that there is a significant difference in comparison with the control. $p < 0.05$.

TABLE 8

| | Thickness of outer nuclear layer (μM) | |
|---|---|---|
| | Lesion | Near optic disk |
| Gum arabic solution (control) | 17.0 ± 5.1 (5) | 25.5 ± 11.5 (5) |
| 1.5% 2-O-octadecyl-ascorbic acid suspension | 16.0 ± 7.2 (5) | 39.0 ± 8.8 (5) |
| 5.0% 2-O-octadecyl-ascorbic acid suspension | 19.2 ± 11.3 (3) | 48.3 ± 1.4 (3) |

Note: In the above table, each value of "thickness of outer nuclear layer" is indicated in terms of mean ± S.D.. The numbers in the parentheses after the values represent the sample numbers.

As is clear from the results shown in Table 7, the thickness of the retinal entire layer near optic disk in the 5.0% 2-O-octadecylascorbic acid suspension administered group is significantly larger than that in the control group. As is clear from the results shown in Table 8, the thickness of the outer nuclear layer near optic disk in the 2-O-octadecylascorbic acid suspension administered groups also tends to be larger than that in the control group.

Table 9 shows the results of the determination of retinal rhodopsin.

TABLE 9

| | Amount of retinal rhodopsin (nM/eye) |
|---|---|
| Gum arabic solution (control) | 0.43 ± 0.19 (5) |
| 1.5% 2-O-octadecyl-ascorbic acid suspension | 0.51 ± 0.20 (5) |
| 5.0% 2-O-octadecyl-ascorbic acid suspension | 0.69 ± 0.14 (3) |

Note: In the above table, each value of "amount of retinal rhodopsin" is indicated in terms of mean ± S.D.. The numbers in the parentheses after the values represent the sample numbers.

As is clear from Table 9, in the determination of retinal rhodopsin in the 2-O-octadecylascorbic acid suspension administered groups, the tendency to inhibit the decrease of the amount of rhodopsin by light exposure was observed.

(B-2) Evaluation by ERG determination (Method 1)

Rats were subjected to dark adaptation for 24 hours. Continuous light exposure for 20 hours was repeated for 3 successive days using a green fluorescent lamp (490–580 nm), the illumination intensity of which was adjusted to 600 to 700 lux. ERG was measured for 3 successive days after dark adaptation for 2 hours after completion of everyday light exposure. After that, the rats were reared in a dark room, and ERG was measured on the 7th day after the light exposure, and evaluated for the amplitude of a-wave and b-wave and the latency of a-wave. From the day before the light exposure, a 5.0% 2-O-octadecylascorbic acid suspension or 5.0% gum arabic solution (control) was orally administered twice a day (200 mg/kg/day) on the day of the light exposure and once a day (100 mg/kg/day) on other days.

Figure 4:
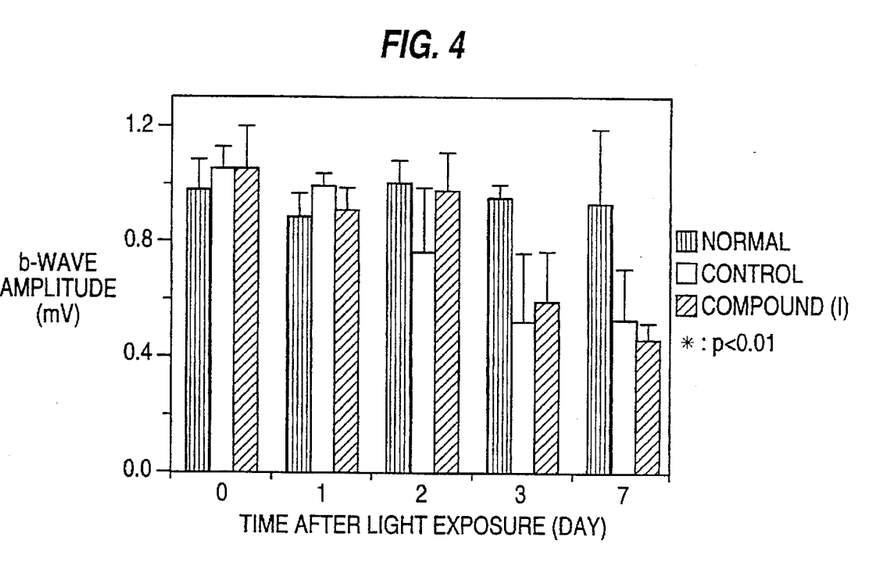
FIG. 4 is a graph showing the b-wave amplitude of ERG in rats after light exposure for 3 days in Experiment 2 (B-2)(Method 1). The abscissa indicates time (day) after light exposure and the ordinate indicates b-wave amplitude (mv).

Results:

The results of the ERG determination in rats after the light exposure for 3 days are shown in FIG. 4 (b-wave amplitude).

As a result, the delay of the a-wave latency and decrease of the a-wave amplitude were observed in the ERG determination on the 1st day. On the 2nd day, the abnormality of a-wave further developed and the decrease of the b-wave amplitude was newly observed. In the 5.0% 2-O-octadecylascorbic acid suspension administered group, the tendency to inhibit the decrease of the b-wave amplitude was observed (cf. FIG. 4). Each wave of ERG was weakened progressively during the continuous light exposure for 3 days. The a-wave latency had been recovered on the 7th day after the light exposure.

(B-2) Evaluation of ERG determination (Method 2)

Rats were subjected to dark adaptation for 12 hours and irradiated with light for 20 successive hours under the same conditions as those of (Method-1). After subjecting them to dark adaptation for 2 hours, ERG was determined. A 5.0% 2-O-octadecylascorbic acid suspension or 5.0% gum arabic solution (control) was orally administered once a day (100 mg/kg/day) from 7 days before the light exposure and twice a day (200 mg/kg/day) only on the day of the light exposure.

Figure 5:
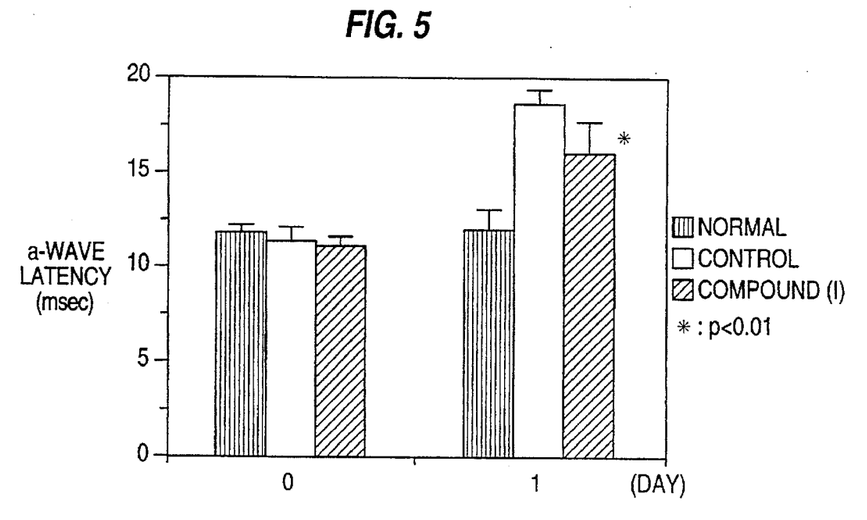
FIG. 5 is a graph showing the a-wave latency of ERG in rats after light exposure for 20 hours in Experiment 2 (B-2)(Method 2). The abscissa indicates time (day) after light exposure and the ordinate indicates a-wave latency (msec).

Results:

The results of the ERG determination in rats after the light exposure for 20 hours are shown in FIG. 5 (a-wave latency).

The amplitude of a-wave and b-wave was decreased in both groups, but the 5.0% 2-O-octadecylascorbic acid suspension administered group significantly inhibited the delay of the a-wave latency (cf. FIG. 5).

Discussion:

The above results show that 2-O-octadecylascorbic acid inhibited disorders of retinal tissues and functions in rats resulting from light exposure. The retinal disorders caused by light in these experiments are severe examples. However, light is one of the risk factors resulting in various retinal metabolic and functional disorders. Therefore, 2-O-octadecylascorbic acid is useful for prevention and treatment of various retinal diseases including retinal vascular disorders and inflammatory or degenerative lesions resulting from systemic diseases such as diabetes, hypertension, arteriosclerosis, anemia, leukemia, connective tissue diseases (e.g., systemic lupus erythematosus, scleroderma, etc.), diseases of congenital metabolism anomaly (e.g., Tay-Sachs diseases, Vogt-Spielmeyer diseases, etc.), retinal local diseases such as retinal vascular disorders (e.g., retinopathy of prematurity, retinal vein obstruction, retinal artery obstruction, retinal periphlebitis, etc.), and, retinal inflammations or degeneration derived from retinal detachment or trauma, retinal degenerative diseases accompanying an aging such as senile disciform macular degeneration, congenital retinal degenerative diseases and the like.

EXPERIMENT 3

Acute toxicity test of 2-O-octadecylascorbic acid

2-O-octadecylascorbic acid was tested for the acute toxicity test in mice. As a result, no mouse died even in oral administration of 1000 mg/kg. This compound has therefore low toxicity.

What is claimed is:

1. A method for treating a retinal disease resulting from ischemia in the eye, selected from the group consisting of diabetes, retinopathy of prematurity, retinal vein obstruction, retinal artery obstruction, retinal detachment and senile disciform macular degeneration, which comprises administering to a subject in need thereof an effective amount of a compound of the formula (I):

wherein n is an integer of 8 to 20.

2. A method according to claim 1, wherein the compound is in a dosage form for oral administration and wherein the administering comprises oral administering.

3. A method according to claim 1, wherein the compound is in a dosage form of tablets and wherein the administering comprises oral administering of the tablets.

4. A method according to claim 1, wherein the compound is in a dosage form of eye drops and wherein the administering comprises administering the eye drops to the subject's eye or eyes.

5. A method according to claim 1, wherein the compound is in a dosage form of ophthalmic ointments and wherein the administering comprises applying the ointment parenterally to the subject.

6. A method according to claim 1, wherein n is 17.

7. A method according to claim 4, wherein the eye drops are sterilized and have a pH value of 4 to 10.

8. A process according to claim 2, wherein the tablets are made by granulating the compound of the formula (I) with a diluent, binder and disintegrator, providing a lubricant to the resultant granules, and compressing into a desired shape and size to obtain tablets.

9. A method according to claim 1, wherein the compound of formula (I) is in the L-isomer form.

10. A method according to claim 4, wherein the eye-drops comprise about 0.001 to 3% (w/v) of compound of the formula (I).

11. A method according to claim 5, wherein the ointment comprises about 0.001 to 3% (w/w) of compound of the formula (I).

* * * * *